US012150883B2

(12) United States Patent
Behn

(10) Patent No.: US 12,150,883 B2
(45) Date of Patent: Nov. 26, 2024

(54) PELVIC PROLAPSE TREATMENT BELT

(71) Applicant: BraceAbility, Inc., Cedar Falls, IA (US)

(72) Inventor: Morgan Jennifer Behn, Cedar Falls, IA (US)

(*) Notice: Subject to any disclaimer, the term of this patent is extended or adjusted under 35 U.S.C. 154(b) by 377 days.

(21) Appl. No.: 17/856,030

(22) Filed: Jul. 1, 2022

(65) Prior Publication Data
US 2022/0331138 A1 Oct. 20, 2022

Related U.S. Application Data

(63) Continuation-in-part of application No. 17/035,464, filed on Sep. 28, 2020, now Pat. No. 11,376,154.

(51) Int. Cl.
A61F 6/14 (2006.01)
A61F 5/28 (2006.01)
A61F 5/30 (2006.01)
A61F 6/08 (2006.01)

(52) U.S. Cl.
CPC . *A61F 5/28* (2013.01); *A61F 5/30* (2013.01)

(58) Field of Classification Search
CPC ...... A61F 6/08; A61F 6/14; A61F 5/28; A61F 5/26; A61F 5/24; A61F 5/37; A61F 5/40; A61F 5/14; A61F 2/0004; A61F 2/0009; A61F 2/0031; A61F 2/0045; A61C 1/08; A61C 1/10; A41D 13/02525; A41B 9/04
See application file for complete search history.

(56) References Cited

U.S. PATENT DOCUMENTS

2019/0029328 A1* 1/2019 Anderson ................. A61F 5/40

* cited by examiner

*Primary Examiner* — Camtu T Nguyen
(74) *Attorney, Agent, or Firm* — Bochner PLLC; Andrew D Bochner

(57) ABSTRACT

A pelvic prolapse treatment belt may include a main structural member having an inner and outer layer. The main structural member may include a plurality of through-hole regions positioned to be located on respective sides of a wearer's spine and a single through hole positioned at an approximate center of a rear of the main structural member. A compression pad may be attached to the main structural member. The compression pad may be configured for placing over a pelvic cavity of the wearer. A single strap may be attached to a bottom end of the compression pad and have a length sufficient for extending over the wearer's intergluteal cleft. The single strap may be sized for inserted through the single through-hole and have a distal end attached to a waist strap. The waist strap may include attachment features for attaching to the outer side of the main structural member.

17 Claims, 14 Drawing Sheets

PELVIC PROLAPSE TREATMENT BELT

FIELD OF THE DISCLOSURE

Disclosed aspects relate to the treatment of pelvic organ prolapse and related conditions.

BACKGROUND

The pelvis (the plural generally called the pelves or pelvises) is either the lower part of the trunk of the human body between the abdomen and the thighs, or the skeleton embedded in it, sometimes also called bony pelvis or pelvic skeleton. The pelvic region of the trunk includes the bony pelvis, the pelvic cavity which is the space enclosed by the bony pelvis, the pelvic floor, below the pelvic cavity, and the perineum below the pelvic floor. The pelvic cavity comprises a meshwork of smooth muscle, ligaments, blood vessels, and connective tissues that attach to the inner walls of the pelvic girdle. The pelvic skeleton is formed in the area of the back, by the sacrum and the coccyx and anteriorly and to the left and right sides, by a pair of hip bones.

The two hip bones connect the spine with the lower limbs. The hip bones are attached to the sacrum posteriorly, connected to each other anteriorly, and joined with the two femurs at the hip joints. The gap enclosed by the bony pelvis, called the pelvic cavity, is the section of the body underneath the abdomen.

FIG. 1 is a lateral view of the anatomy of a normal female's pelvic cavity shown as 100, where none of the organs of the female pelvic cavity 100 are shown prolapsed. The pubic bone 105 is shown as well as the pelvic floor muscle 108 located at the bottom of the pelvic cavity 100 which supports the contents of the pelvis comprising the female pelvic organs. The female pelvic organs are shown as the bladder 121 coupled to urethra 122, the uterus 131 that is coupled to the cervix 132 which is coupled to the vagina 133, and the rectum 141 that is coupled to the anus 142.

The pelvic floor muscle 108 being at the base of the pelvic cavity 100 assists in supporting all of these organs to prevent prolapse. However, one or more of the uterus 131, vagina 133, anus 142, urethra 122, bladder 121, cervix 132, and the small bowel can prolapse in a condition commonly referred to as pelvic organ prolapse (POP).

POP generally relates to a condition where the muscles including the pelvic floor muscle 108 and ligaments supporting a woman's pelvic organs weaken enough to allow one or more of the pelvic area organ(s) to slip out of their normal place (and thus to prolapse). There are different types of POP, including vaginal vault prolapse, bladder prolapse also known as cystocele prolapse, rectal prolapse, uterine prolapse, urethral prolapse, cervical prolapse, and small bowel prolapse.

In certain cases, POP occurs due to the damage of the pelvic floor muscle 108 and its associated tissue that supports the intra-abdominal contents causing the contents of the abdominal cavity to extend through the weakest support points and extrude through the vaginal walls. This weakness can be at the bladder area, the uterine area, or the rectal/enterocele area. The POP condition can worsen over time, and the patient may thus eventually need corrective surgery to remedy this condition.

POP is generally treated by invasive methods comprising surgical implants generally including meshes which may be applied in combination with sutures to hold the mesh in place. Alternatively, POP can be treated with sutures that close the parted pelvic floor muscle and associated tissues in a known "non-mesh" technique. Meshes are usually applied in open surgical procedures, although meshes may sometimes be applied in laparoscopic surgical procedures.

SUMMARY

This Summary is provided to introduce a brief selection of disclosed concepts in a simplified form that are further described below in the Detailed Description including the drawings provided. This Summary is not intended to limit the claimed subject matter's scope.

An aspect of the present disclosure may include a pelvic prolapse treatment belt. The pelvic prolapse treatment belt may include a main structural member having an inner layer and an outer layer. The main structural member may have a length adapted to wrap around a wearer including being configured for after the wearer steps into the pelvic prolapse treatment belt for pulling the main structural member up to hips of the wearer. The main structural member may include a plurality of through-hole regions adapted to be positioned on respective sides of a spine of the wearer. The pelvic prolapse treatment belt may further include a compression pad having a top end and a bottom end, the top end may be attached to the main structural member and adapted to extend over a pelvic floor muscle and associated tissue of the wearer; an outer pad adapted to be placed over the compression pad; a single strap having a first end and a second end, the first end may be attached to the bottom end, the single strap may have a length adapted to extend over an intergluteal cleft of the wearer; and a waist strap having an attachment feature at each of opposing ends, the waist strap may be disposed between the inner layer and the outer layer of the main structural member and may extend out of at least two through-holes located on opposing sides of the main structural member. The single strap may be adapted to be inserted through a single through-hole located at an approximate center of a rear of the main structural member, and may have a distal end opposite the bottom end, the distal end may be attached to the waist strap. The waist strap may be configured for pulling and then attaching each of the attachment features to the outer layer of the main structural member.

In an embodiment, the outer pad may be placed over the compression pad and the outer pad may be softer than the compression pad. The outer pad may be attached to the main structural member. The outer pad may fully encase the compression pad, and the outer pad may comprise at least one of nylon, polyester, satin, spandex, rayon, and cotton.

In another embodiment, the main structural member may further include an extension segment, a hook tab, and a loop strip. The hook tab may be located at one end of the extension segment, and the loop strip may be located at the opposite end of the extension segment.

In yet another embodiment, the compression pad may comprise a foam material having a minimum porosity of at least 25%, and a thickness between 1 mm and 6 mm. The foam material may comprise a rigid foam material having a Young's modulus in compression of at least 2 MPa at room temperature In a further embodiment, the single strap or waist strap may comprise an elastomeric material, and may have a length to width ratio of 10:1 to 50:1.

In an embodiment, each attachment feature may comprise hooks or loops, and the outer layer of the main structural member may include an other of the hooks or loops.

In another embodiment, a top portion of the compression pad may have a tapered shape.

An aspect of the present disclosure may include a method of treating pelvic prolapse. The method may include providing a pelvic prolapse treatment belt comprising a main structural member having an inner layer and an outer layer. The main structural member may have a length adapted to wrap around a wearer. The main structural member may include a plurality of through-hole regions adapted to be positioned on respective sides of a spine of the wearer. The pelvic prolapse treatment belt may further include a compression pad attached to the main structural member. The compression pad may be adapted to extend over a pelvic floor muscle and associated tissue of the wearer. The pelvic prolapse treatment belt may further include a single strap having a first end and a second end, the first end may be attached to the bottom end. The single strap may have a length adapted to extend over an intergluteal cleft of the wearer. The pelvic prolapse treatment belt may yet further include a waist strap having an attachment feature at each of opposing ends. The waist strap may be disposed between the inner layer and the outer layer of the main structural member and may extend out of at least two through-holes located on opposing sides of the main structural member. The single strap may be adapted to be inserted through a single through-hole located at an approximate center of a rear of the main structural member, and may have a distal end opposite the bottom end, the distal end may be attached to a waist strap. The waist strap may be configured for pulling and then attaching each of the attachment features to the outer layer of the main structural member. The method may further include stepping into the pelvic prolapse treatment belt; pulling the main structural member up to hips of the wearer; pulling each of the opposing ends of the waist strap such that the compression pad applies an upward and inward pressure on the pelvic floor muscle and associated tissue; and after the pulling, attaching the respective attachment features of the waist strap to the outer side of the main structural member.

In an embodiment, the attachment feature may comprise hooks or loops, and the outer side of the main structural member may include an other of the hooks or loops.

In another embodiment, the outer pad may be placed over the compression pad and the outer pad may be softer than the compression pad. The outer pad may be attached to the main structural member. The outer pad may fully encase the compression pad. The outer pad may comprise nylon, polyester, satin, or cotton.

In yet another embodiment, the main structural member further includes an extension segment, a hook tab, and a loop strip. The hook tab may be located at one end of the extension segment, and the loop strip may be located at the opposite end of the extension segment. In such an embodiment, the method may further include after pulling the main structural member up to hips of the wearer, pulling the hook tab, and attaching the hook tab to the loop strip.

In a further embodiment, the compression pad comprises a foam material that has a thickness between 1 mm and 6 mm.

In an embodiment, a top portion of the compression pad may have a tapered shape.

In an aspect of the present disclosure, the pelvic prolapse treatment belt may include a main structural member having an inner layer, an outer layer, an extension segment, a hook tab, and a loop strip. The main structural member may have a length adapted to wrap around a wearer including being configured for after the wearer steps into the pelvic prolapse treatment belt for pulling the main structural member up to hips of the wearer. The main structural member may include a plurality of through-hole regions adapted to be positioned on respective sides of a spine of the wearer. The hook tab may be located at one end of the extension segment, and the loop strip may be located at the opposite end of the extension segment. The pelvic prolapse treatment belt may further include a compression pad having a top end and a bottom end, the top end may be attached to the main structural member and adapted to extend over a pelvic floor muscle and associated tissue of the wearer; an outer pad adapted to be placed over the compression pad; a single strap having a first end and a second end, the first end may be attached to the bottom end, the single strap may have a length adapted to extend over an intergluteal cleft of the wearer; and a waist strap having an attachment feature at each of opposing ends, the waist strap may be disposed between the inner layer and the outer layer of the main structural member and may extend out of at least two through-holes located on opposing sides of the main structural member. The single strap may be adapted to be inserted through a single through-hole located at an approximate center of a rear of the main structural member, and may have a distal end opposite the bottom end, the distal end may be attached to the waist strap. The waist strap may be configured for pulling and then attaching each of the attachment features to the outer layer of the main structural member.

DETAILED DESCRIPTION

Figure 1:
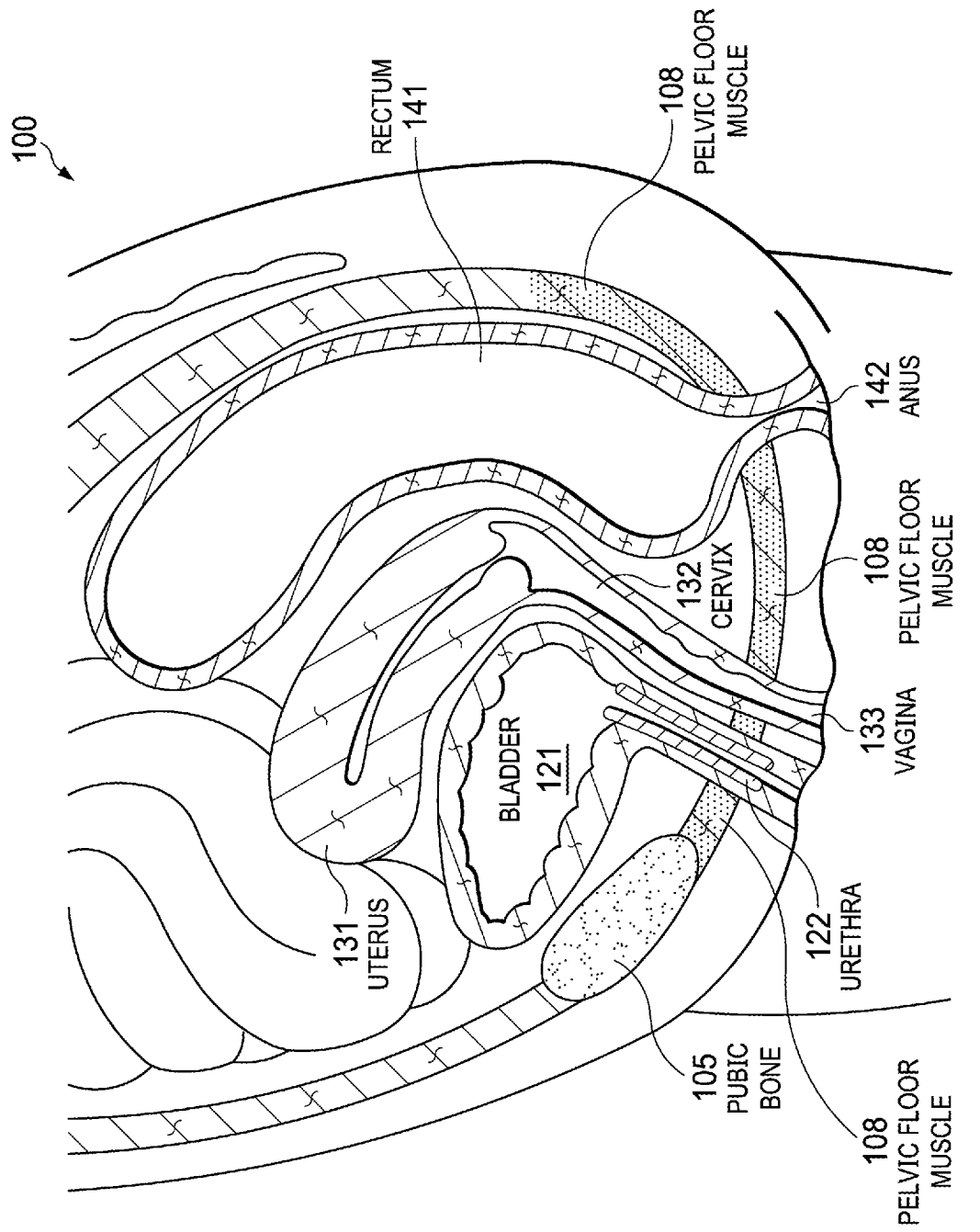
FIG. 1 is a lateral view of the anatomy of a normal female pelvic cavity, where none of the organs within the female pelvic cavity are shown prolapsed.

Disclosed aspects are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed aspects.

Figure 2A:
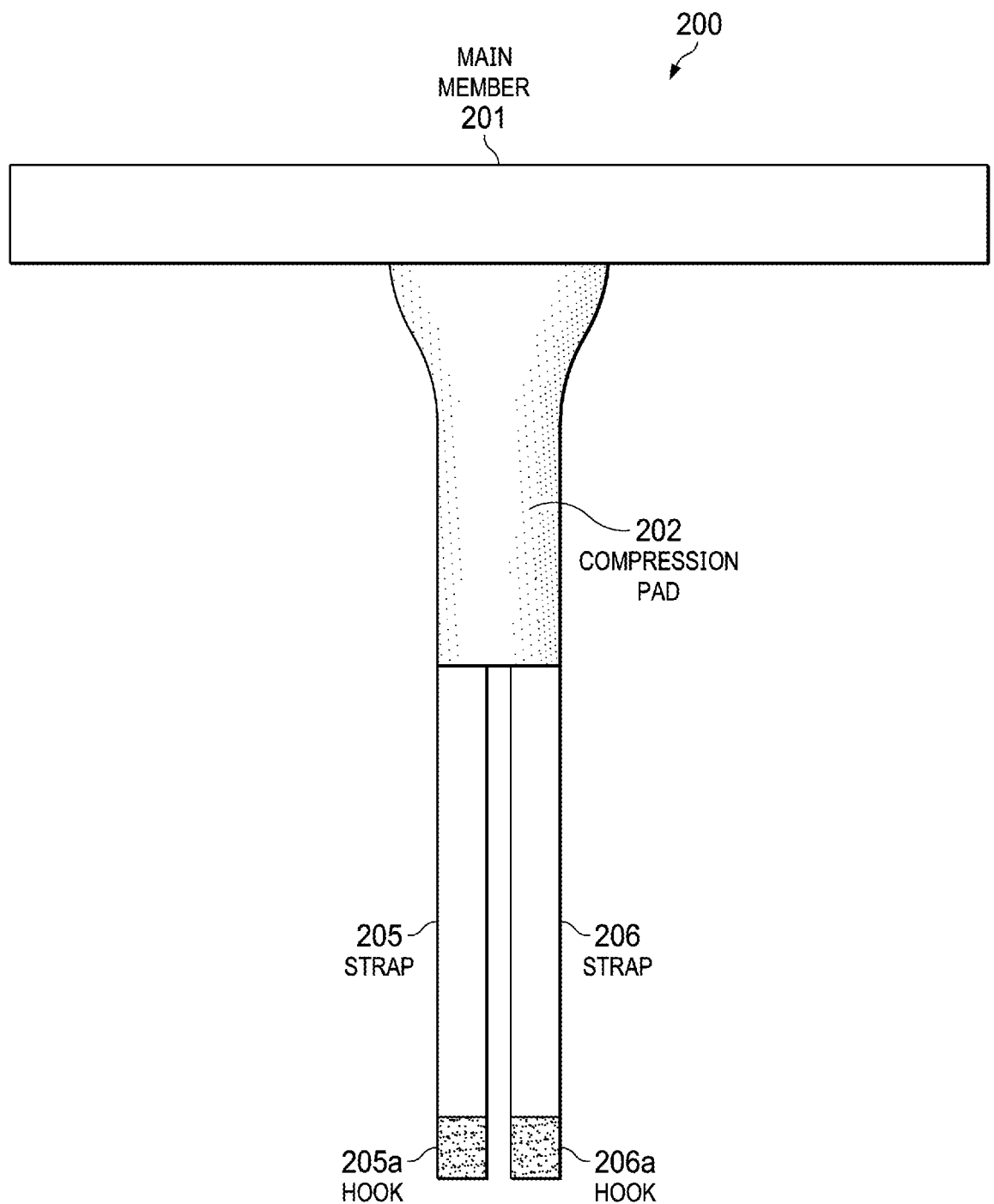
FIG. 2A is a front-view depiction an example pelvic prolapse prevention belt laying out flat, thus not on a wearer, showing a compression pad with a first strap and a second strap attached to the bottom of the compression pad. Although the pelvic prolapse prevention belt has through-holes in the main structural member, they are not shown in FIG. 2A, nor in FIG. 2B described below, due to these both of these FIGS. being front-views.
Figure 2B:
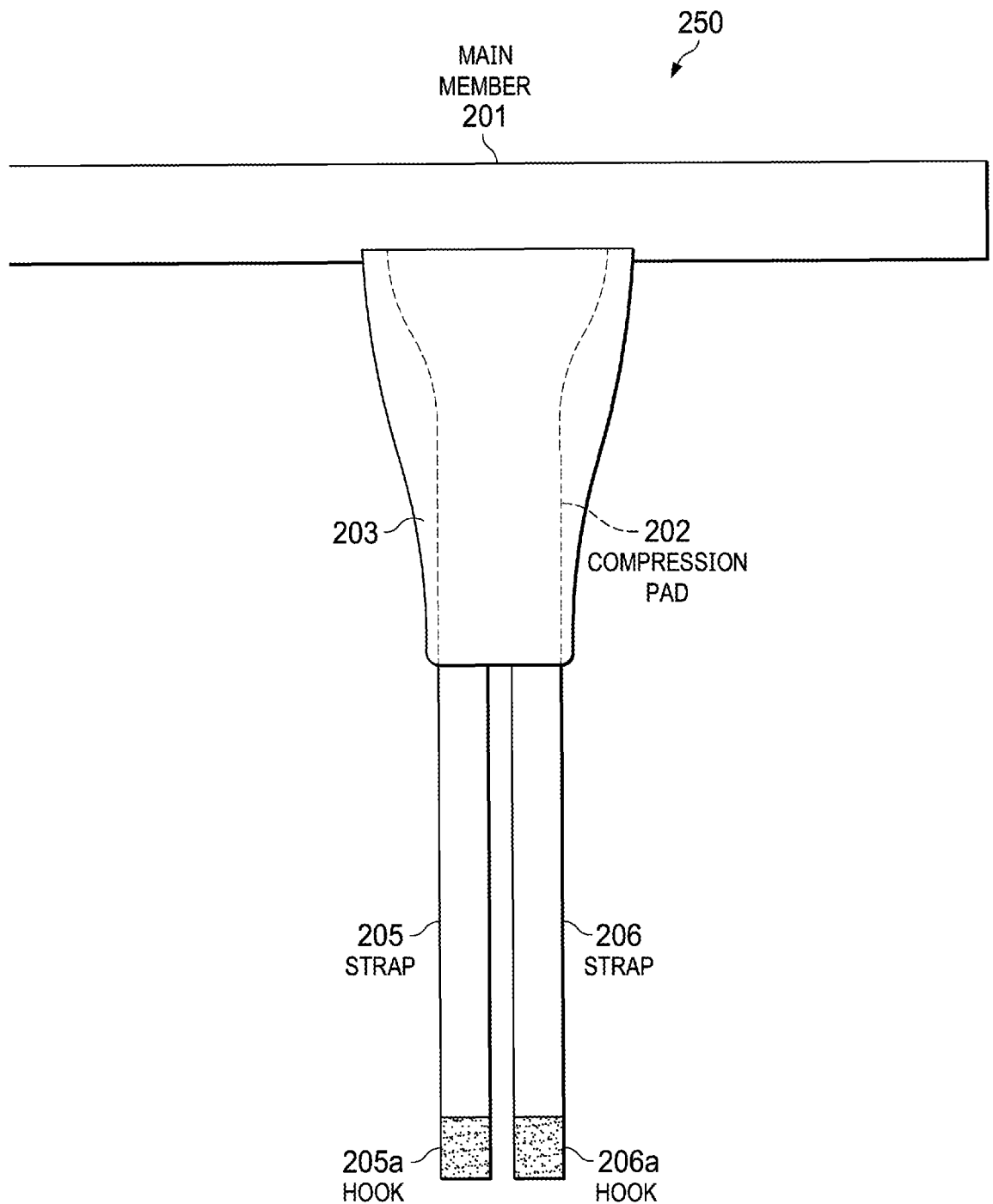
FIG. 2B is a front-view depiction an example pelvic prolapse prevention belt laying out flat, showing an outer pad over a compression pad, according to an example aspect.

FIG. 2A is a front-view depiction of an example pelvic prolapse prevention belt 200 laying out flat, showing a compression pad 202 with a first strap 205 and a second strap 206 both attached to the bottom of the compression pad 202. There is shown a first hook 205a on the distal end of the first strap 205, and a second hook 206a on the distal end of the second strap 206. Alternatively, one or both of the hooks 205a, 206a shown can be replaced by loops. FIG. 2B is a front-view depiction an example pelvic prolapse prevention belt 250 laying out flat, having all the features shown in the pelvic prolapse prevention belt 200 shown in FIG. 2A, but also having an outer pad 203 shown as an optional feature over the compression pad 202.

The compression pad 202 can comprise a foam material having a minimum porosity of at least 25%, such as having a porosity from 25% to 90%, and having a thickness between 1 mm and 6 mms. The compression pad 202 is shown having a tapered shape with its top portion being the widest. Although the pelvic prolapse prevention belt 200 has through-holes in the main structural member 201, as noted above, they are not shown in FIG. 2A, nor in FIG. 2B described below, due to these FIGS. being front-views.

The main structural member 201 has an inner side and an outer side that has a length sufficient for wrapping around wearer, and is configured for after a wearer steps into the belt for pulling the main structural member 201 up to their hips. The main structural member 201 generally has a width between 1 and 5 inches.

Figure 2C:
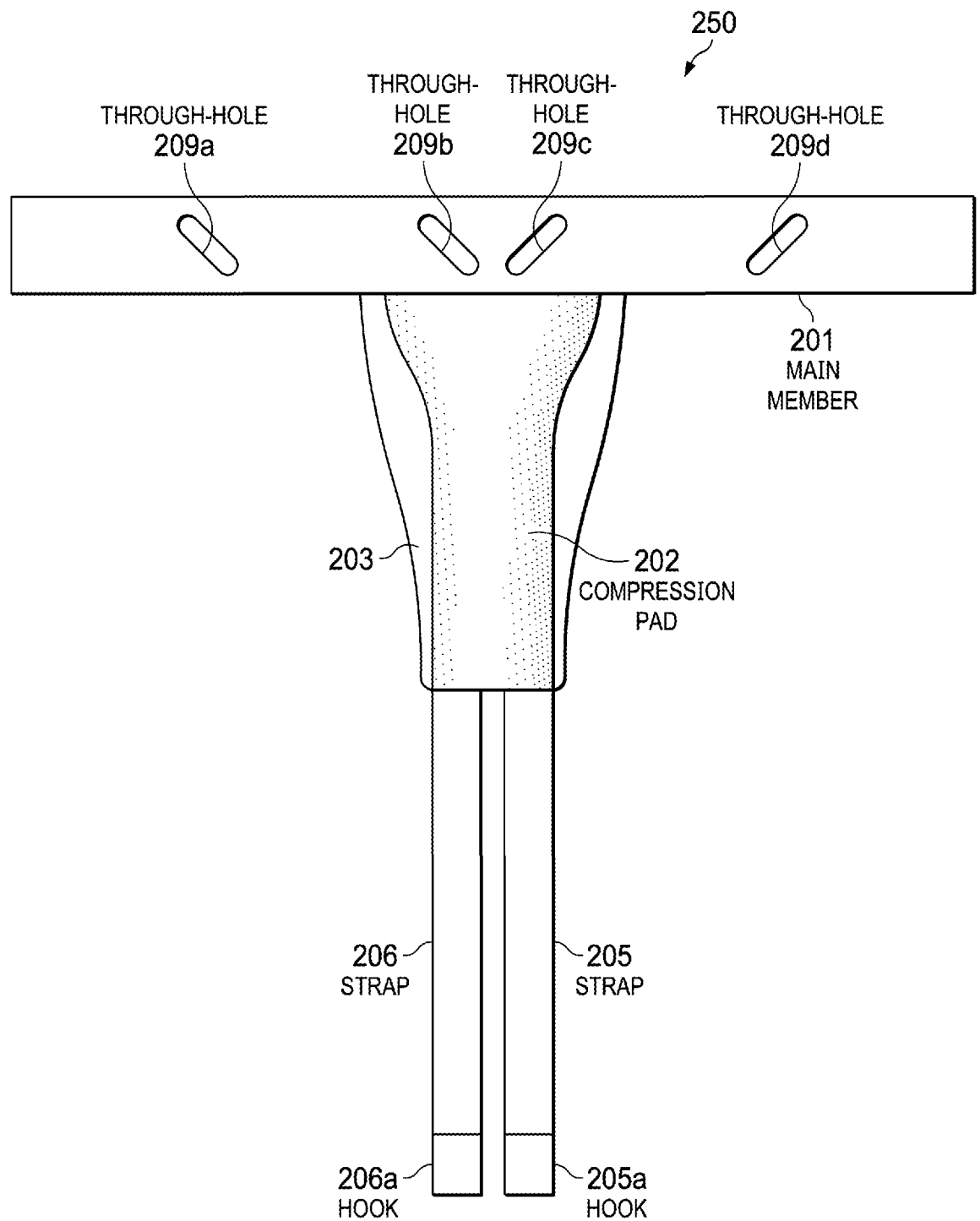
FIG. 2C shows a back-view depiction of the pelvic prolapse prevention belt shown in FIG. 2B, again laying out flat, showing a plurality of through-holes formed through the main structural member, with the straps attached to the bottom of the compression pad and/or the outer pad, according to an example aspect.

FIG. 2C shows a back-view depiction of the example pelvic prolapse prevention belt 250 shown in FIG. 2B having the outer pad 203 over the compression pad 202 that can encase the compression pad 202, again laying out flat, now showing a plurality of through-holes 209a, 209b, 209c, and 209d (two through-holes on each side), thus being through a full thickness of the main structural member 201. The outer pad 203 can comprise for example nylon, polyester, satin, spandex, rayon, cotton, or a mixture of these. There may be more than two through-holes on each side of the belt, such as 3, 4, or 5 through-holes on each side of the main structural member 201, although there are generally 2 to 4 through-holes on each side of the belt.

Disclosed through-holes can comprise grommets, buttonhole openings, slits, or die-cut holes. A grommet is known to be a ring or edge strip inserted into a hole through thin material, typically a sheet of textile fabric, sheet metal, composite of carbon fiber, wood, or honeycomb. Grommets are generally flared or collared on each side to keep them in place and are commonly made from metal, plastic, or rubber. The through-holes 209a-209d are generally within a distance of 10" (inches) to the right side and left side of the wearer's spine.

The location of the through-holes 209a-209d allows the wearer to decide the placement of the straps 205, 206 therethrough, and thus the level of pressure applied, for their individual comfort. The straps 205, 206, 212, 216 can comprise an elastomeric material and can have a length to width ratio of 10:1 to 50:1. The straps 205, 206 each get pulled by the wearer through one of the through-holes 209a-209d which as described above creates leverage, allowing the wearer to (by choosing from the available through-holes 209a-209d on each side) to increase or decrease the amount of upward and inward pressure they apply to their pelvic floor muscle and its associated tissue by the compression pad 202.

The compression pad 202 and/or the outer pad 203 is attached the main structural member 201, such as by stitching or by an adhesive, and the compression pad 202 is configured to be positioned between the wearer's legs, over their pelvic floor muscle and associated tissue, thus for being placed on top of and thus structurally supporting the wearer's prolapsed organ(s). The first strap 205 and a second strap 206 are attached to the bottom of the compression pad 202 and/or the outer pad 203.

The straps 205, 206 have sufficient length to extend over the buttocks of the wearer, then through any of the through-holes 209a-d on the main structural member 201, and then finally to attach to an attachment feature (such as loops in the case of hooks 205a, 206a) provided by the main structural member 201. As noted above, the straps 205, 206 function for adjusting (for tightening and or loosening) the upward and inward pressure on the pelvic floor muscle and associated tissue received from the compression pad 202. The straps 205, 206 when placed through a through-hole 209a-209d each create leverage, allowing the wearer to tighten or loosen the amount of upward and inward pressure they feel on their pelvic floor muscle from the compression pad 202.

The main structural member 201 can be formed from a single material or a mixture of two or more different materials. The material for the main structural member 201 can be selected from elastomeric or non-elastomeric materials. For example, the main structural member 201 can comprise neoprene that can have hooks or loops (the opposite of what is on the distal end the straps 205, 206 shown by example as hooks 205a, 206a) to attach to after being directed be the wearer through a respective through-hole 209a-209d in the main structural member 201 shown in FIG. 2C to be one part of a hook-based fastener arrangement. Neoprene is known to be a family of synthetic rubbers produced by polymerization of chloroprene, where neoprene is known to exhibit good chemical stability and maintains flexibility over a wide temperature range. A known hook and loop-based arrangement is VELCRO, or a similar fastening mechanism may also be used.

The outer pad 203 comprises a soft material as compared to the material of the compression pad 202. As noted above the compression pad 202 can comprise a foam material. The foam material can comprise a rigid foam defined herein to have a Young's modulus in compression of at least 2 MPa at room temperature, typically in the range of 2 to 50 MPa. The compression pad 202 can comprise in one specific example a breathable foam (a rigid foam such as extruded polystyrene (XPS) or a polyurethane foam) in the density range of 0.04 to 3.5 grams per cubic centimeter. Both open cell and closed cell foams are both generally possible. Besides a foam, the compression pad can 202 can comprise a more rigid material such as hard plastic, rubber, or silicone. The compression pad 202 can have a thickness between 1 mm and 6 mm. Other materials for the compression pad 202 may include a spacer fabric (spacer fabrics are known to be a kind of 3D manufactured textile structures in which two outer fabric layers are connected by a layer of pile threads), mesh, or neoprene (rubber).

The outer pad 203 has a thickness that is generally 0.2 mm to 3 mm. The outer pad 203 can comprise materials including nylon, polyester, satin, or cotton, with the material being a soft material generally being selected for the comfort of the wearer.

The outer surface of the main structural member 201 can include loops or hooks, such as in the case of loops the loops can comprise unbreakable durability loop fabric (UBL) for the purpose of attaching hooks to the hooks 205a, 206a of the straps 205, 206, 216. The inside surface of the main structural member 201 generally comprises a soft fabric such as nylon, polyester, satin, or cotton. Sewn or otherwise attached such as using hooks and loops to the outside of the lower portion of the main structural member 201 can be the outer pad 203 which can encase the compression pad 202.

The compression pad 202, or the compression pad 202 having an outer pad 203, generally has a shape that tapers from being relatively wide at the top to the being relatively narrow bottom, generally by a 35% to a 70% reduction in width, in one arrangement forming a triangle-like shape in roughly the top half. The tapered shaped portion, such as being substantially triangular in shape, with a wider top as compared to the bottom enables fitting correctly over the pelvic floor muscle and its associated tissue of the wearer and through the disclosed strapping system comprising the straps 205, 206, and the through-holes 209a-209d, for providing adequate upward and inward directed pressure.

Sewn or otherwise attached to the narrower end of the outer pad 203 are a first strap 205 and a second strap 206. The straps 205, 206, 212, and 216 generally comprise an elastomeric material and are generally sized with a maximum length to width ratio of 50:1. An elastomer as known in chemical arts is a polymer with viscoelasticity (i.e., both viscosity and elasticity) that has very weak intermolecular forces, generally low Young's modulus, and high failure strain compared with other materials. IUPAC (The International Union of Pure and Applied Chemistry) defines the term "elastomer" by a "polymer that displays rubber-like elasticity." The straps 205, 206, 212, and 216 can also comprise a non-elastomeric material. Non-elastomeric material for the straps can include non-stretch nylon, cotton, and polyester.

The straps 205, 206 can be sewn on side-by-side to the bottom of the compression pad 202 and/or the outer pad 203. The respective ones of the straps 205, 206 on the wearer's left and right side, respectively, are for placing through a through-hole 209c or 209d for the first strap 205, and through-hole 209a or 209b for the second strap 206, of the wearer's choosing provided on the back of the main structural member 201. The straps 205, 206, 216 are for feeding from the inside of the main structural member 201 to the outside of the main structural member 201 through one of the through-holes 209a-209d on each side of the belt of the wearer's choice.

Once the respective straps are fed through their wearer' selected through-hole 209a-209d on each side of the pelvic prolapse prevention belt, the wearer takes the first strap 205 which when on their right into their right hand, and the second strap 206 when on their left end into their left hand, and then pulls them towards the front of the pelvic prolapse prevention belt which causes the compression pad 202 and/or the outer pad 203 to create upward and inward pressure to the pelvic floor muscle and its associated tissue thus pushing against the prolapsed organ(s). The wearer then attaches the attachment features shown by example hooks 205a, 205b on the distal ends of the respective straps 205, 206 to the outside surface of main structural member 201, such as using a hook and loop attachment, for example, VELCRO.

The pelvic prolapse prevention belt is applied by a wearer in essentially the same manner as pulling up underwear. The wearer steps into the pelvic prolapse prevention belt 200 or 250 and pulls the main structural member 201 up to their hips. The pelvic prolapse prevention belt can be worn over or under any garment.

The first and second straps 205, 206 are then extended over a buttocks of the wearer so that the compression pad 202 (with an optional outer pad 203 thereon) is over the pelvic floor muscle and associated tissue of the wearer. After the extending of the first and second straps 205, 206, the first and the second straps 205, 206 are directed through ones of the through-holes 209a-209d by feeding the first and the second straps 205, 206 through from an inside to and outside of the through-holes 209a-209d. The straps 205, 206 are thus fed by the wearer through selected ones of the available through-holes 209*a*-209*d* of the main structural member 201 on respective sides of the wearer's spine.

The through-holes 209*a*-209*d* are generally placed within 10 inches to each side of the wearer's spine to create an upward and inward directed pressure to the pelvic floor muscle and its associated tissue when the straps 205, 206, 216 are fed through the through-holes 209*a*-209*d* of the wearer's choosing from the inside of the main structural member 201 to the outside. The wearer then pulls the straps 205, 206, 216 towards the front of their body to obtain the desired tension level, thus, creating a user personalized or user-controlled upward and inward pressure onto their prolapsed organ(s). After the pulling, the wearer then attaches the straps 205, 206, 216 to an attachment feature (such as loops) on the outer side of the main structural member 201.

Figure 3:
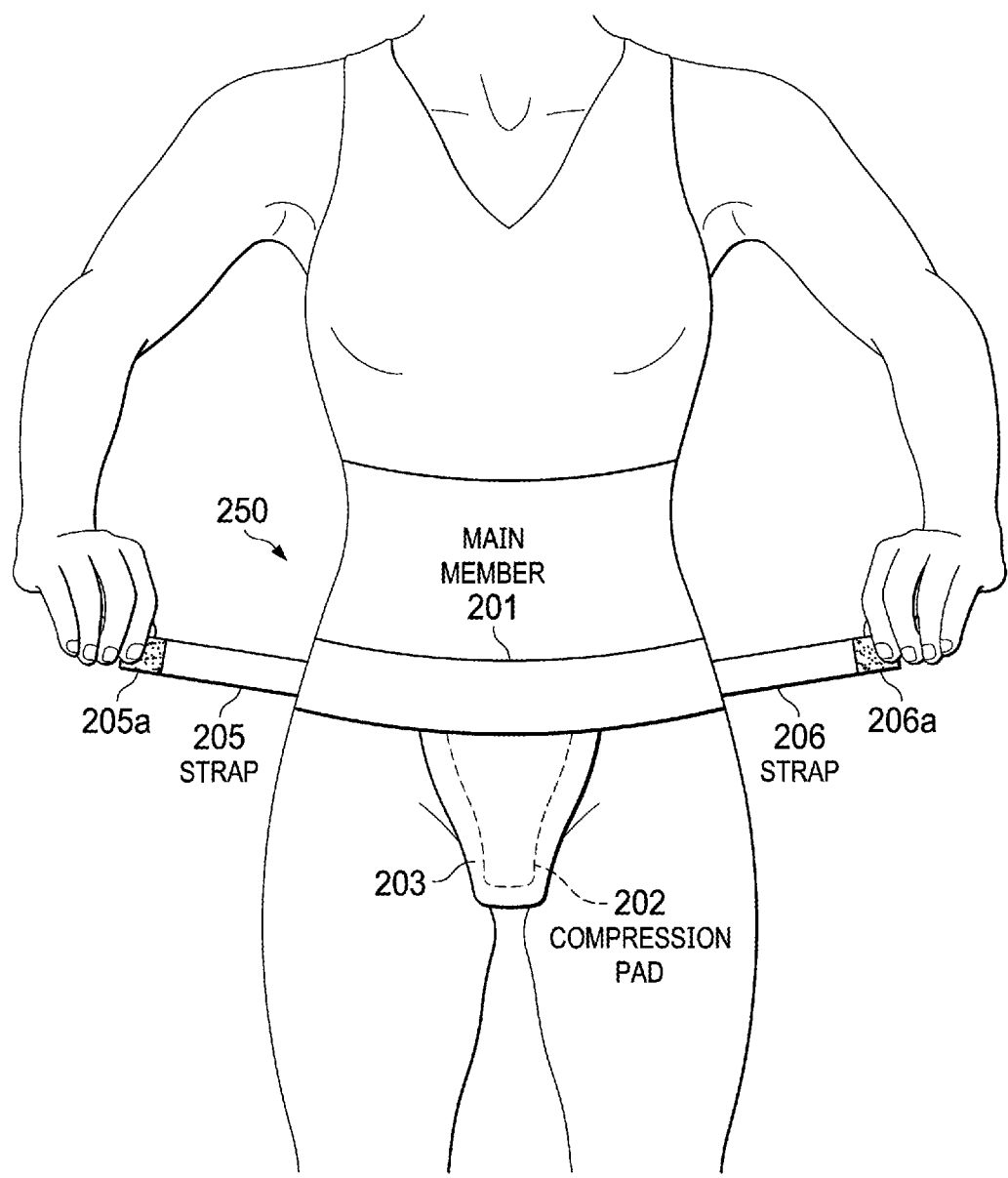
FIG. 3 shows an example of a front-view depiction of a wearer having the disclosed pelvic prolapse prevention belt's shown in FIG. 2B main structural member positioned around their hips with the compression pad shown positioned on their pelvic floor muscle and associated tissue, with the wearer holding one strap in her left hand and the other strap in her right hand, according to an example aspect.

FIG. 3 shows an example of a front-view depiction of a wearer having the disclosed pelvic prolapse prevention belt's 250 main structural member 201 positioned around their hips with the compression pad 202 having its outer pad 203 thereon shown positioned on their pelvic floor muscle and associated tissue. The wearer is shown holding the second strap 206 in her left hand and the first strap 205 in her right hand. As described below, the wearer then attaches the hooks 205*a*, 206*a* on the ends of the straps 205, 206 to a suitable attachment feature on the main structural member 201.

Figure 4:
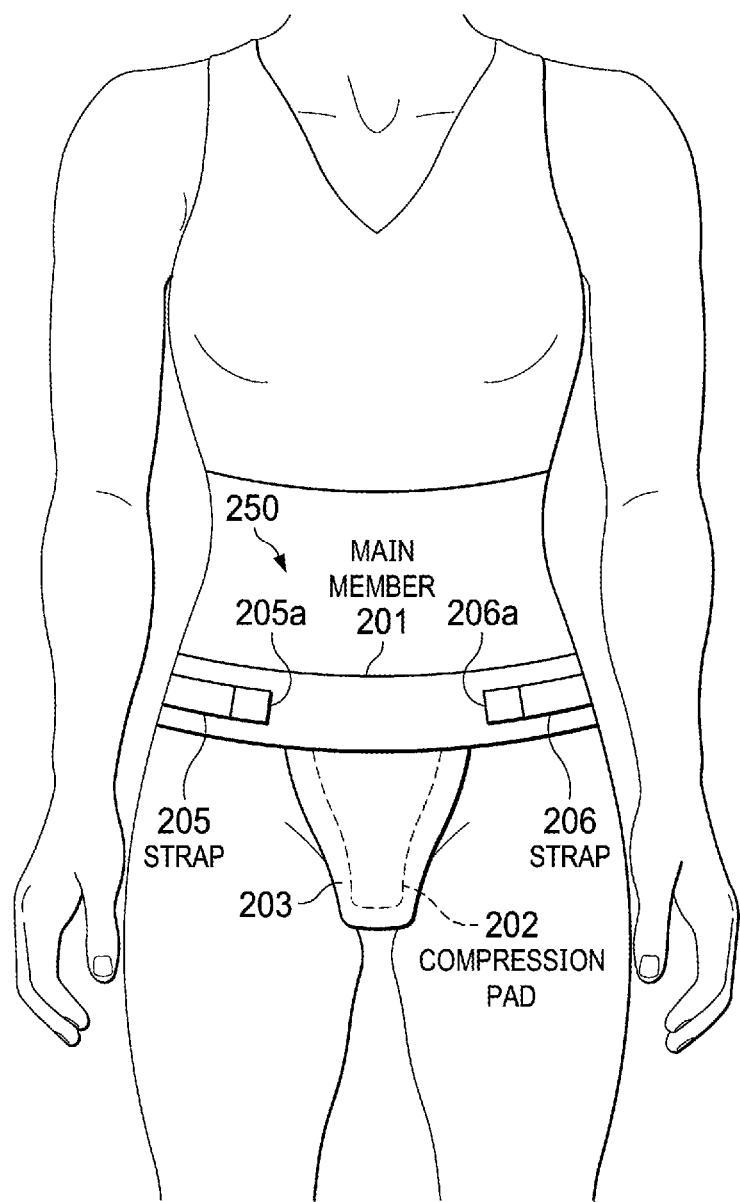
FIG. 4 shows an example of a front-view depiction of a wearer having the disclosed pelvic prolapse prevention belt's shown in FIG. 2B main structural member positioned around their hips with the compression pad on their pelvic cavity including over their pelvic floor muscle and associated tissue, with the straps now fastened with their hooks to respective sides of the main structural member which may have loops, according to an example aspect.

FIG. 4 shows an example of a front-view depiction of a wearer having the disclosed pelvic prolapse prevention belt's 250 main structural member 201 positioned around their hips with the compression pad 202 having its outer pad 203 thereon shown positioned on their pelvic floor muscle and associated tissue, with the respective straps 205, 206 now fastened with their hooks 205*a* and 206*a* attached to attachment features located on respective sides of the main structural member 201, according to an example aspect. In this arrangement where the straps 205, 206 include hooks 205*a* and 206*a*, the main structural member 201 may have loops.

Figure 5:
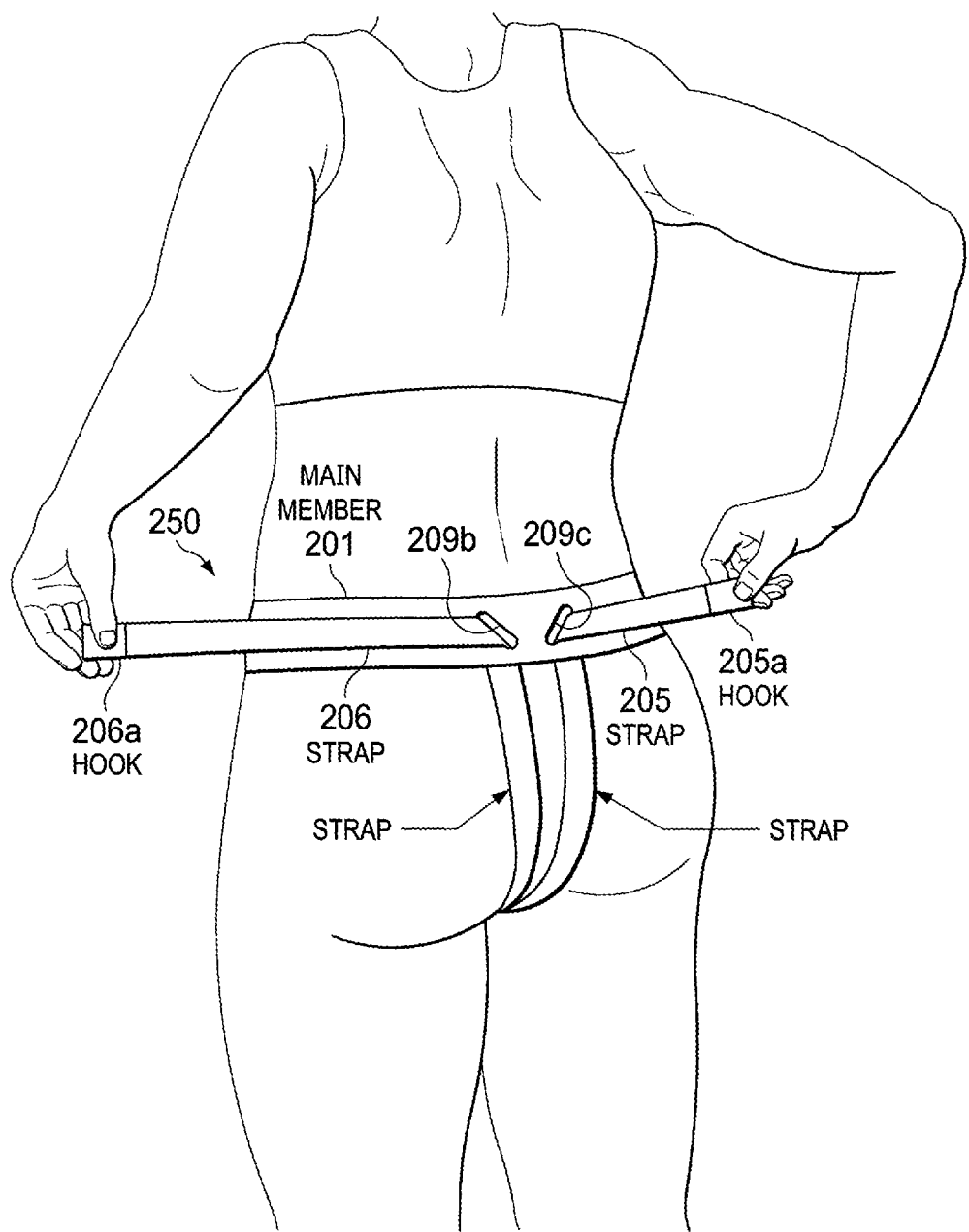
FIG. 5 shows an example of a back-view depiction of a wearer having the disclosed pelvic prolapse prevention belt's shown in FIG. 2B main structural member positioned around their hips, with the straps fed through the center two through-holes, with the wearer holding one strap in her left hand and the other strap in her right hand, according to an example aspect.

FIG. 5 shows an example of a back-view depiction of a wearer having the disclosed pelvic prolapse prevention belt's 250 main structural member 201 positioned around their hips, with the straps 205, 206 fed through the center two through-holes shown as 209*b* and 209*c* according to an example aspect. Regarding FIG. 5, as well as FIGS. 6-8 described below, the outer pad 203 shown for the pelvic prolapse prevention belt 250 in FIGS. 2B, 2C, 3, and 4 cannot be seen from these back-views. The compression pad 202, and when present the outer pad 203 over the compression pad 202, cover the pelvic cavity/pelvic floor muscle, but do not extend up over the buttock, making them non-visible from a back-view. The wearer is shown holding the first strap 205 in her right hand and the second strap 206 in her left hand.

Figure 6:
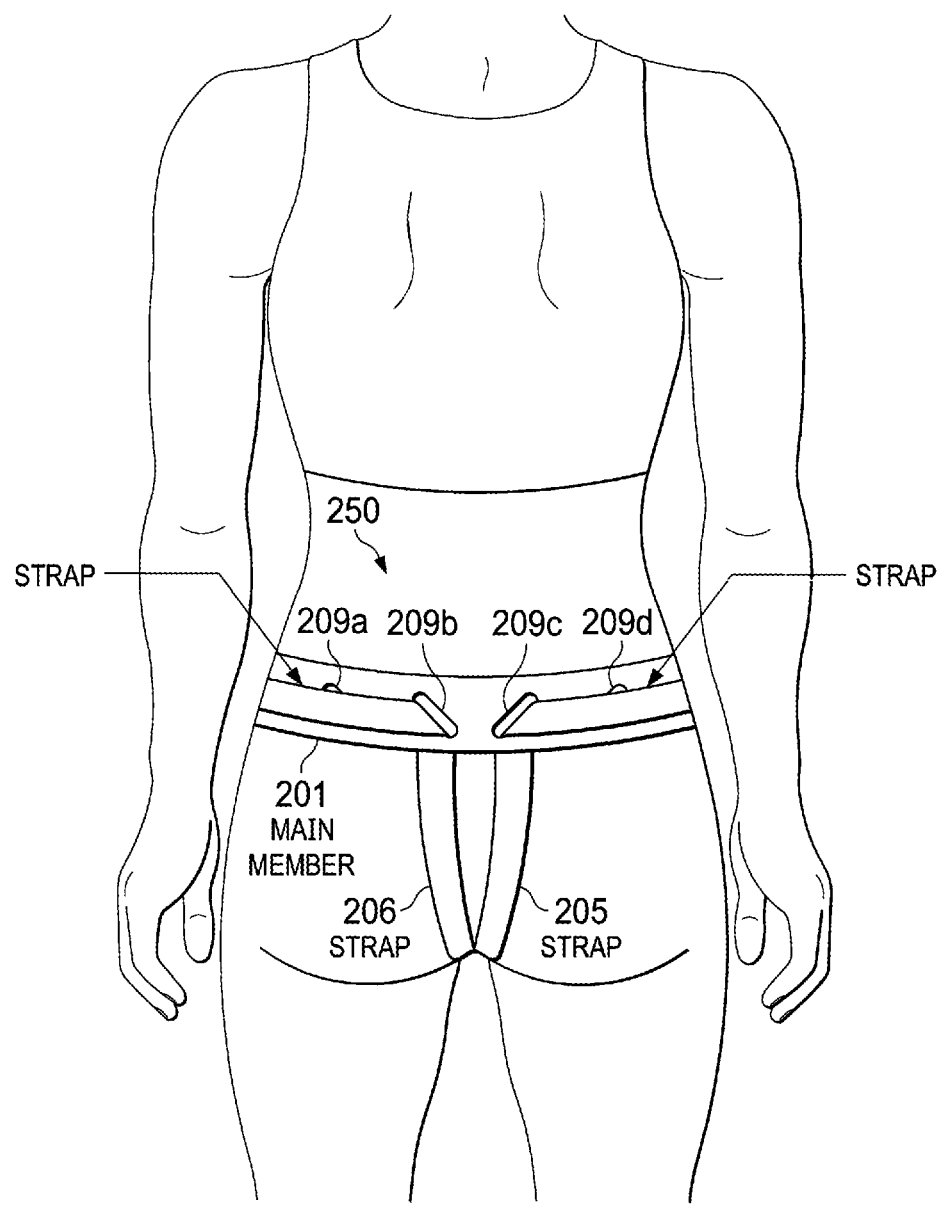
FIG. 6 shows an example of a back-view depiction of a wearer having the disclosed pelvic prolapse prevention belt's shown in FIG. 2B main structural member positioned around their hips, with the straps fed through the center two through-hole now attached to the main structural member, such as using a hooks and loops-based attachment, according to an example aspect.

FIG. 6 shows an example of a back-view depiction of a wearer having the disclosed pelvic prolapse prevention belt's 250 main structural member 201 positioned around their hips, with the straps 205, 206 fed through the center two through-hole shown as 209*b* and 209*c* now attached to the main structural member 201, according to an example aspect. For example, the straps 205, 206 can be attached to the main structural member 201 using a hooks and loops-based fastener arrangement.

Figure 7:
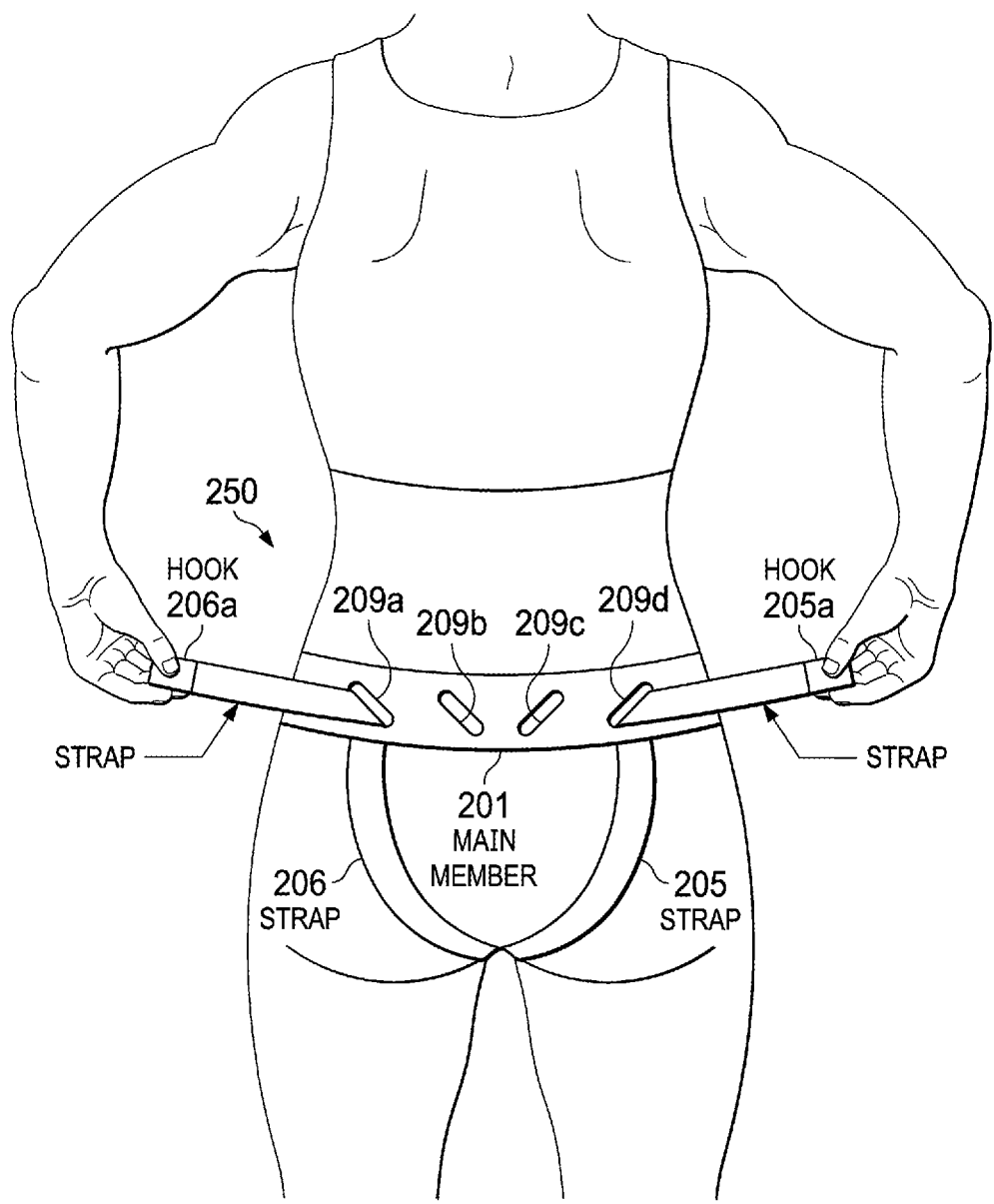
FIG. 7 shows an example of a back-view depiction of a wearer having the disclosed pelvic prolapse prevention belt's shown in FIG. 2B main structural member positioned around their hips, with the straps fed through the outer ones of through-holes on each side, with the wearer holding one strap in her left hand and the other strap in her right hand, according to an example aspect.
Figure 8:
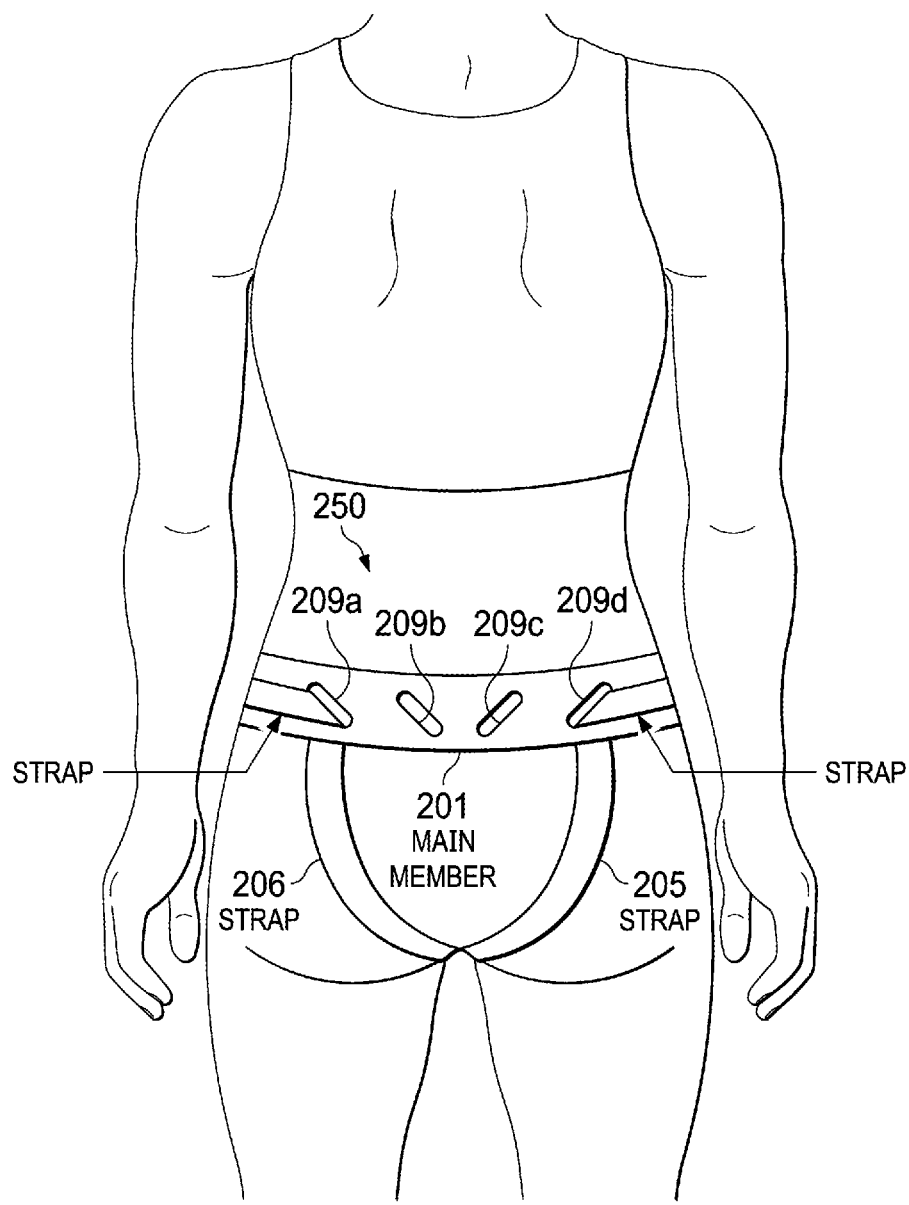
FIG. 8 shows an example of a back-view depiction of a wearer having the disclosed pelvic prolapse prevention belt's shown in FIG. 2B main structural member positioned around their hips, with the straps fed through the outer two through-holes, and now attached to the main structural member using a hooks and loops-based attachment, according to an example aspect.
Figure 9:
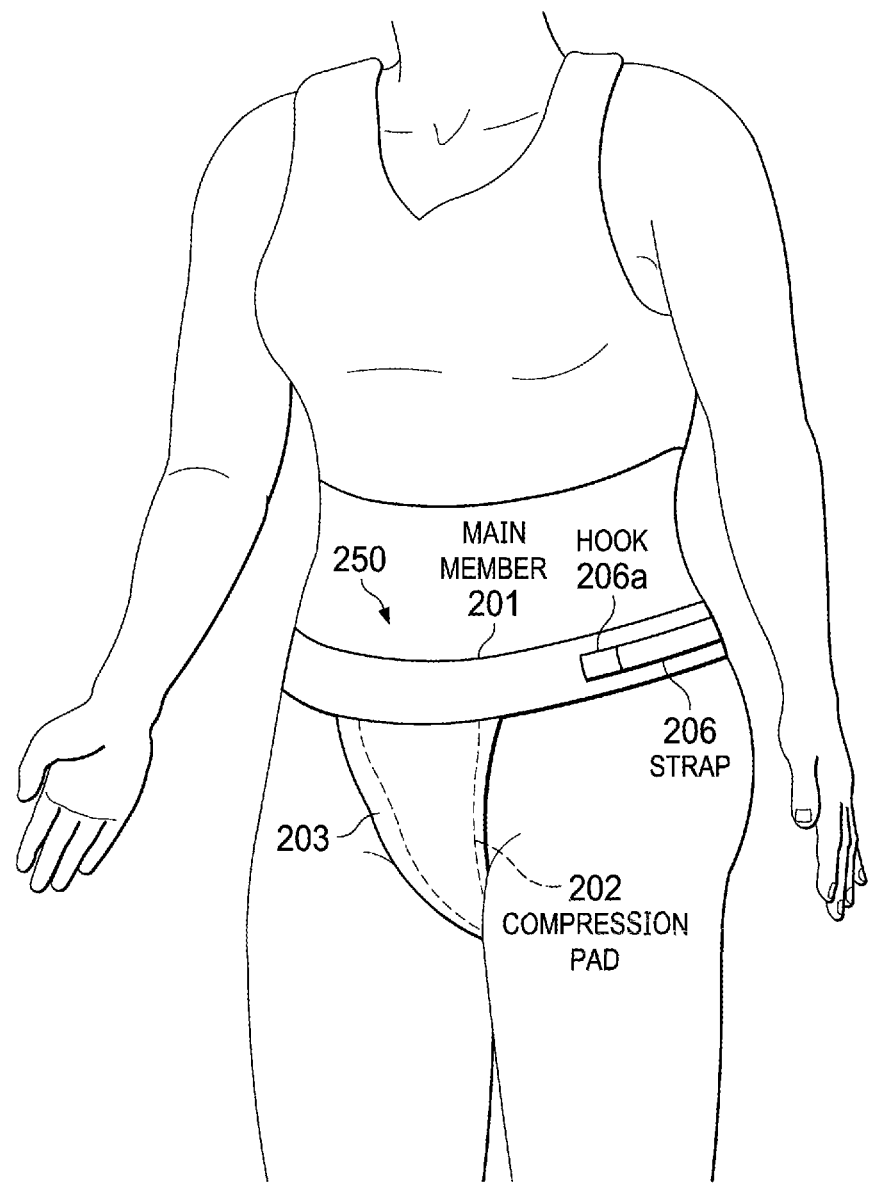
FIG. 9 shows an example of a side-view depiction of a wearer having the disclosed pelvic prolapse prevention belt's shown in FIG. 2B main structural member positioned around their hips with the compression pad on their pelvic floor muscle and associated tissue, with one strap fastened to the main structural member using a hooks and loops-based attachment, according to an example aspect.

FIG. 7 shows an example of a back-view depiction of a wearer having the disclosed pelvic prolapse prevention belt's 250 main structural member 201 positioned around their hips, with the straps 205, 206 fed through the outer ones of the through-holes on each side shown as 209*a* and 209*d*, respectively, holding the first strap 205 in her right hand and the second strap 206 in her left hand, according to an example aspect. FIG. 8 shows an example of a back-view depiction of a wearer having the disclosed pelvic prolapse prevention belt's 250 main structural member 201 positioned around their hips, with the straps 205, 206 fed through the outer two through-holes shown as 209*d* and 209*a*, respectively, and now attached to the main structural member 201 using hooks and loops, according to an example aspect. FIG. 9 shows an example of a side-view depiction of a wearer having the disclosed pelvic prolapse prevention belt's 250 main structural member 201 positioned around their hips with the compression pad 202 and outer pad 203 on their pelvic floor muscle and associated tissue, with the left strap 206 fastened to the main structural member 201 using hooks and loops, according to an example aspect.

Figure 10:
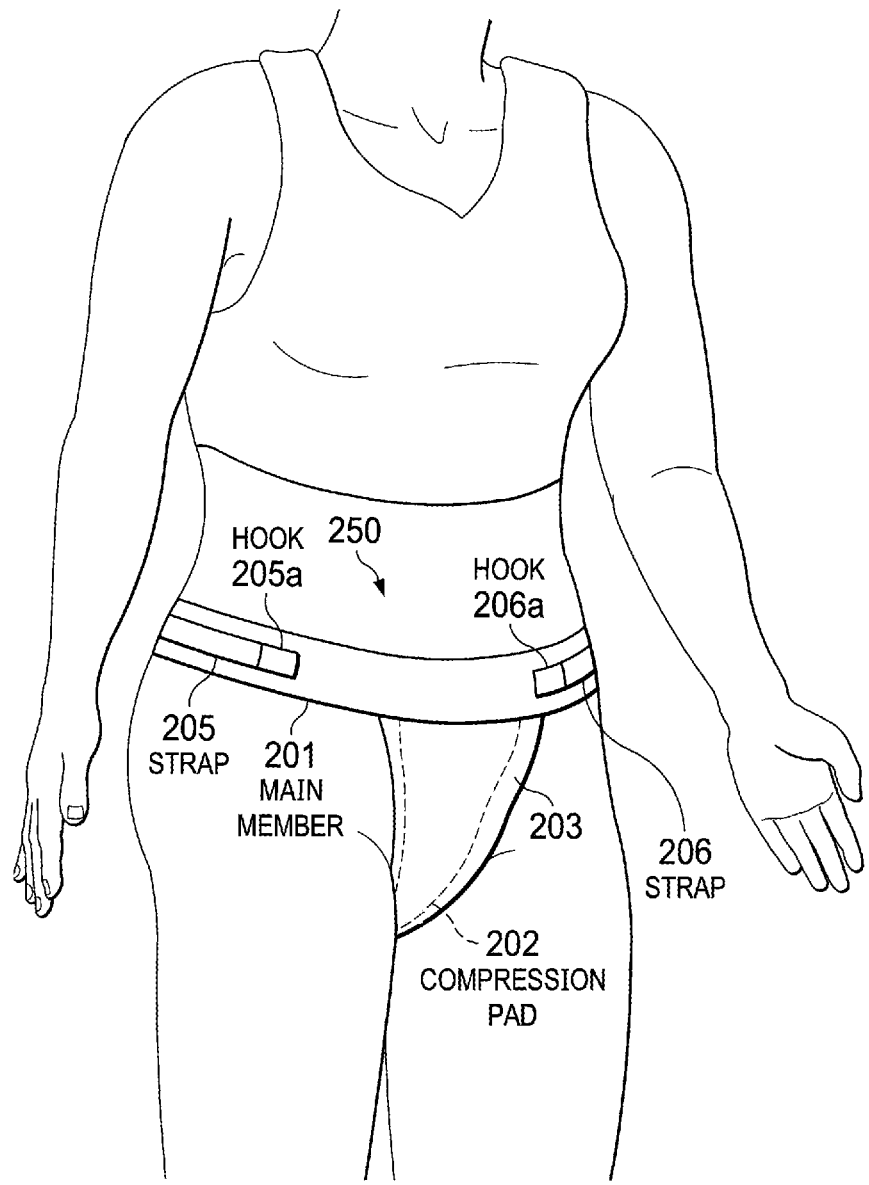
FIG. 10 shows an example of a side-view depiction of the wearer having the disclosed pelvic prevention prolapse belt's shown in FIG. 2B main structural member positioned around their hips with the compression pad on their pelvic floor muscle and associated tissue, with both straps fastened to the main structural member using a hooks and loops-based attachment, according to an example aspect.

FIG. 10 shows an example of a side-view depiction of the wearer having the disclosed pelvic prevention prolapse belt's 250 main structural member 201 positioned around their hips with the compression pad 202 and outer pad 203 on their pelvic floor muscle and associated tissue, with both straps 205, 206 fastened to the main structural member 201 using hooks and loops.

Figure 11:
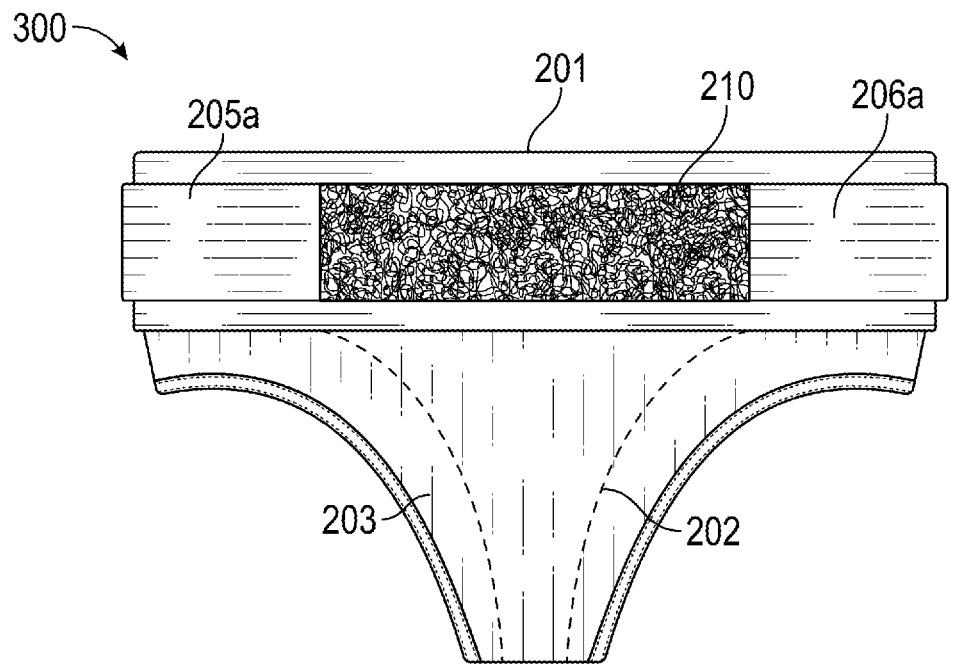
FIG. 11 shows a front-view depiction of an example pelvic prolapse prevention belt laying out flat.

FIG. 11 is a front-view depiction of an example pelvic prolapse prevention belt 300 laying out flat, showing the outer pad 203 attached to the main structural member 201. As evidenced by FIG. 11, the pelvic prolapse prevention belt 300 may be designed to resemble ordinary women's underwear. In an embodiment, the outer pad 203 functions to cover the compression pad 202 but may also encase the compression pad 202 as discussed in greater detail below. The main structural member 201 may include one or more loop strips 210 disposed across a portion of the main structural member 201. The one or more loop strips 210 may interface with one or both of the hooks 205*a*, 206*a*. Alternatively, the one or more loop strips 210 may include hooks instead of loops, and one or both of the hooks 205*a*, 206*a* may include loops instead of hooks.

Figure 12:
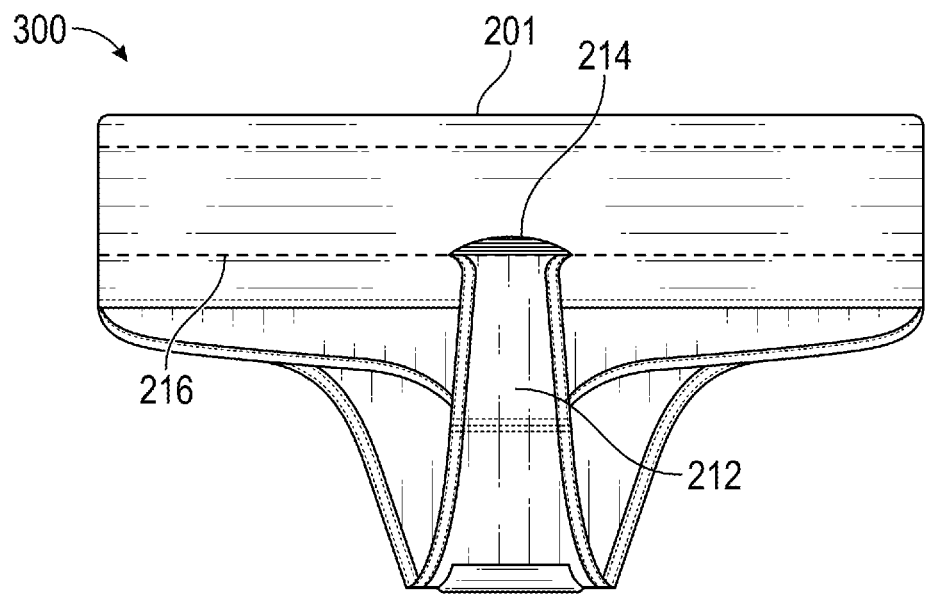
FIG. 12 shows a rear-view depiction of an example pelvic prolapse prevention belt laying out flat.

FIG. 12 is a rear-view depiction of an example pelvic prolapse prevention belt 300 laying out flat. In an embodiment the pelvic prolapse prevention belt 300 includes a single strap 212 attached to the bottom of the compression pad 202. In an embodiment, the single strap 212 has a length adapted to extend over an intergluteal cleft of the wearer. The single strap 212 may be attached to the bottom of the compression pad 202 via stitching, adhesive, or by any other suitable means of attachment. The main structural member 201 may include a single through-hole 214 passing through a full thickness of the main structural member 201. The single through-hole 214 may be positioned on the outer surface of the main structural member 201 at an approximate position along a vertical axis of symmetry dissecting the pelvic prolapse prevention belt 300. However, the single through-hole 214 may be positioned at any suitable location. In an embodiment, the single through-hole is sized to accept the single strap 212.

The single strap 212 may be attached to a waist strap 216. In an embodiment, the waist strap 216 comprises a first and second waist strap 216. In such an embodiment, the single strap 212 extends through the single through-hole 214, where the first and second waist straps 216 are attached to opposing sides of the single strap 212, extending outwardly therefrom. The waist strap 216 may be adapted to extend around a waist of the wearer on either side. The waist strap 216 may be partially encased within the main structural member 201, and extending through through-holes 109*a*, and 109*d*. In such an embodiment, the main structural member 201 may include an inner layer and an outer layer. The inner and outer layers may be attached along their respective top and bottom edges. In further accordance with this embodiment, a portion of the waist strap 216 may be partially disposed between the inner and outer layer of the main structural member 201. In yet further accordance with this embodiment, the single through-hole 214, and through holes 209a and 209d, may be configured to pass through only a full thickness of the outer layer of the main structural member 201.

Figure 13:
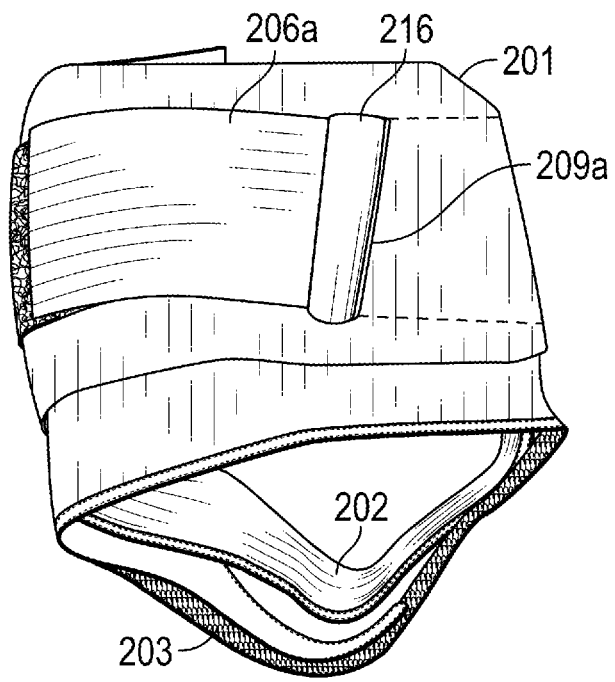
FIG. 13 shows a side-view depiction of an example pelvic prolapse prevention belt.

As exemplified in FIG. 13, each end of the waist strap 216 may be fed through a wearer's selected through-hole 209a, 209d on each side of the pelvic prolapse prevention belt 300, the wearer may take the first hook 205a, and the second hook 206a, and then pull the hooks 205a, 206a towards the front of the pelvic prolapse prevention belt 300 which causes the compression pad 202 and/or the outer pad 203 to create upward and inward pressure to the pelvic floor muscle and its associated tissue thus pushing against the prolapsed organ(s). The wearer then attaches the attachment features shown by example hooks 205a, 205b on each end of the waist strap 216 to the outside surface of main structural member 201, such as using a hook and loop attachment, for example, VELCRO, to attach to the one or more loop strips 210.

As shown in FIG. 13, the compression pad 202 may be separate from the outer pad 203. In another embodiment, the outer pad 203 encases the compression pad 202. In such an embodiment, the outer pad 203 may comprise at least two pieces of material attached along the perimeter, with the compression pad 202 disposed within the space therein between the at least two pieces of material of the outer pad 203. The at least two pieces of material of the outer pad 203 may be attached using adhesive, stitching, or any suitable attachment method.

Figure 14:
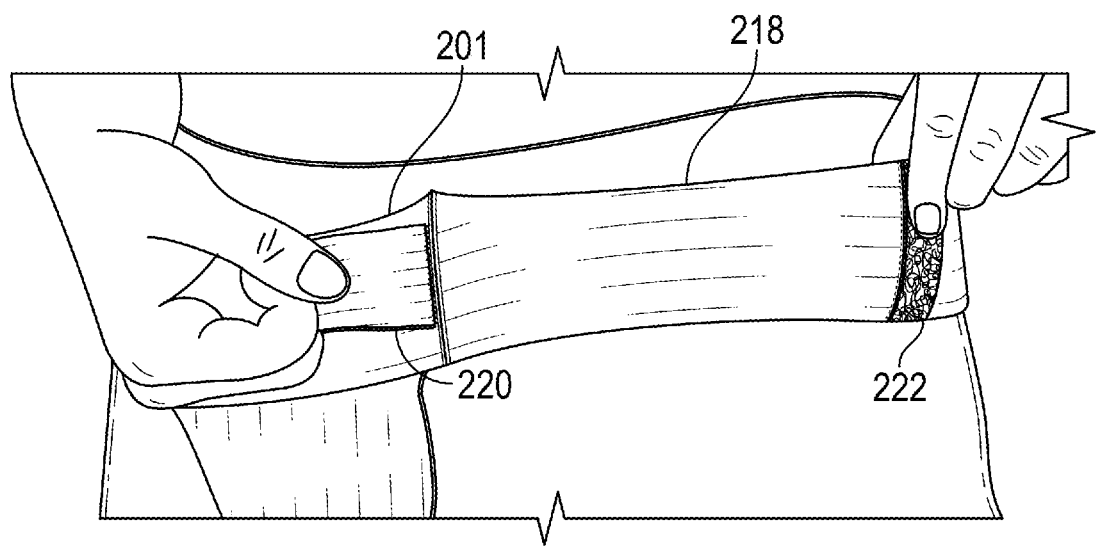
FIG. 14 shows an example of a side-view depiction of a wearer having the disclosed pelvic prolapse prevention belt's main structural member 201 positioned around their hips according to various aspects of the present disclosure.

FIG. 14 shows an example of a side-view depiction of a wearer having the disclosed pelvic prolapse prevention belt's 200, 250, 300 main structural member 201 positioned around their hips with the compression pad 202 having its outer pad 203 thereon shown positioned on their pelvic floor muscle and associated tissue. As shown in FIG. 14, in an embodiment of the present disclosure, the main structural member includes one or more extension segments 218. In an embodiment, there is an extension segment 218 located along the main structural member 201 at the left and right side of the wearer when the pelvic prolapse prevention belt 200, 250, 300 is worn. Each extension segment 218 may be constructed using an elastomeric material. However, a non-elastomeric material may be used. The extension segment 218 may be a portion of the main structural member having greater elasticity than the remaining material of the main structural member 201, allowing for a looser fit of the main structural member 201 when the extension segment 218 is in an extended state. The extension segment 218 may be positioned at any suitable point along the main structural member 201. When in the extended state, the looser fit of the main structural member 201 allows the wearer to more easily step into, and pull up, the pelvic prolapse prevention belt 200, 250, 300, before tightening the main structural member 201 against the wearer's waist.

To allow a wearer to adjust the tightness of the main structural member 201, the main structural member 201 may include a hook tab 220 located at either end of the extension segment 218. At the end opposite the end of the extension segment 218 having the hook tab 220, the main structural member 201 may include a loop strip 222. In such an embodiment, after a wearer steps into the belt, and pulls the main structural member 201 up to their hips, the wearer may pull the hook tab 220 and attach it to the loop strip 222 at the opposite end of the extension segment 218, thus tightening the main structural member 218 around the wearer's waist.

While various disclosed aspects have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The invention claimed is:

1. A pelvic prolapse treatment belt, comprising:
    a main structural member having an inner layer and an outer layer, the main structural member having a length adapted to wrap around a wearer including being configured for after the wearer steps into the pelvic prolapse treatment belt for pulling the main structural member up to hips of the wearer, wherein the main structural member includes a plurality of through-hole regions adapted to be positioned on respective sides of a spine of the wearer;
    a compression pad having a top end and a bottom end, the top end attached to the main structural member and adapted to extend over a pelvic floor muscle and associated tissue of the wearer;
    an outer pad adapted to be placed over the compression pad;
    a single strap having a first end and a second end, the first end attached to the bottom end, the single strap has a length adapted to extend over an intergluteal cleft of the wearer; and
    a waist strap having an attachment feature at each of opposing ends, the waist strap disposed between the inner layer and the outer layer of the main structural member and extending out of at least two through-holes located on opposing sides of the main structural member,
        wherein the single strap is adapted to be inserted through a single through-hole located at an approximate center of a rear of the main structural member, and has a distal end opposite the bottom end, the distal end attached to the waist strap, and
        wherein the waist strap is configured for pulling and then attaching each of the attachment features to the outer layer of the main structural member.

2. The pelvic prolapse treatment belt of claim 1, wherein the outer pad is placed over the compression pad and the outer pad is softer than the compression pad, wherein the outer pad is attached to the main structural member.

3. The pelvic prolapse treatment belt of claim 2, wherein the outer pad fully encases the compression pad, and wherein the outer pad comprises at least one of nylon, polyester, satin, spandex, rayon, and cotton.

4. The pelvic prolapse treatment belt of claim 1, wherein the main structural member further includes an extension segment, a hook tab, and a loop strip,
    wherein the hook tab is located at one end of the extension segment, and the loop strip is located at the opposite end of the extension segment.

5. The pelvic prolapse treatment belt of claim 1, wherein the compression pad comprises a foam material having a minimum porosity of at least 25%, and a thickness between 1 mm and 6 mm.

6. The pelvic prolapse treatment belt of claim 5, wherein the foam material comprises a rigid foam material having a Young's modulus in compression of at least 2 MPa at room temperature.

7. The pelvic prolapse treatment belt of claim 1, wherein the single strap or waist strap comprises an elastomeric material, and has a length to width ratio of 10:1 to 50:1.

8. The pelvic prolapse treatment belt of claim 1, wherein each attachment feature comprises hooks or loops, wherein the outer layer of the main structural member includes an other of the hooks or loops.

9. The pelvic prolapse treatment belt of claim 1, wherein a top portion of the compression pad has a tapered shape.

10. A method of treating pelvic prolapse, comprising:
providing a pelvic prolapse treatment belt comprising a main structural member having an inner layer and an outer layer, the main structural member has a length adapted to wrap around a wearer, the main structural member including a plurality of through-hole regions adapted to be positioned on respective sides of a spine of the wearer, a compression pad attached to the main structural member, the compression pad adapted to extend over a pelvic floor muscle and associated tissue of the wearer, a single strap having a first end and a second end, the first end attached to the bottom end, the single strap has a length adapted to extend over an intergluteal cleft of the wearer, and a waist strap having an attachment feature at each of opposing ends, the waist strap disposed between the inner layer and the outer layer of the main structural member and extending out of at least two through-holes located on opposing sides of the main structural member, wherein the single strap is adapted to be inserted through a single through-hole located at an approximate center of a rear of the main structural member, and has a distal end opposite the bottom end, the distal end attached to the waist strap, and wherein the waist strap is configured for pulling and then attaching each of the attachment features to the outer layer of the main structural member;
stepping into the pelvic prolapse treatment belt;
pulling the main structural member up to hips of the wearer;
pulling each of the opposing ends of the waist strap such that the compression pad applies an upward and inward pressure on the pelvic floor muscle and associated tissue; and
after the pulling, attaching the respective attachment features of the waist strap to the outer side of the main structural member.

11. The method of claim 10, wherein the attachment feature comprises hooks or loops, wherein the outer side of the main structural member includes an other of the hooks or loops.

12. The method of claim 10, wherein the outer pad placed over the compression pad and the outer pad is softer than the compression pad, wherein the outer pad is attached to the main structural member.

13. The method of claim 12, wherein the outer pad fully encases the compression pad, and wherein the outer pad comprises nylon, polyester, satin, or cotton.

14. The method of claim 10, wherein the main structural member further includes an extension segment, a hook tab, and a loop strip,
wherein the hook tab is located at one end of the extension segment, and the loop strip is located at the opposite end of the extension segment, and
wherein the method further includes:
after pulling the main structural member up to hips of the wearer, pulling the hook tab, and attaching the hook tab to the loop strip.

15. The method of claim 10, wherein the compression pad comprises a foam material that has a thickness between 1 mm and 6 mm.

16. The method of claim 10, wherein a top portion of the compression pad has a tapered shape.

17. A pelvic prolapse treatment belt, comprising:
a main structural member having an inner layer, an outer layer, an extension segment, a hook tab, and a loop strip, the main structural member having a length adapted to wrap around a wearer including being configured for after the wearer steps into the pelvic prolapse treatment belt for pulling the main structural member up to hips of the wearer, wherein the main structural member includes a plurality of through-hole regions adapted to be positioned on respective sides of a spine of the wearer;
wherein the hook tab is located at one end of the extension segment, and the loop strip is located at the opposite end of the extension segment;
a compression pad having a top end and a bottom end, the top end attached to the main structural member and adapted to extend over a pelvic floor muscle and associated tissue of the wearer;
an outer pad adapted to be placed over the compression pad;
a single strap having a first end and a second end, the first end attached to the bottom end, the single strap has a length adapted to extend over an intergluteal cleft of the wearer; and
a waist strap having an attachment feature at each of opposing ends, the waist strap disposed between the inner layer and the outer layer of the main structural member and extending out of at least two through-holes located on opposing sides of the main structural member,
wherein the single strap is adapted to be inserted through a single through-hole located at an approximate center of a rear of the main structural member, and has a distal end opposite the bottom end, the distal end attached to the waist strap, and
wherein the waist strap is configured for pulling and then attaching each of the attachment features to the outer layer of the main structural member.

* * * * *